United States Patent
Gunday et al.

(10) Patent No.: US 9,629,979 B2
(45) Date of Patent: Apr. 25, 2017

(54) PRESSURE/VACUUM ACTUATED CATHETER DRUG DELIVERY PROBE

(75) Inventors: Erhan H. Gunday, Great Neck, NY (US); Lawrence J. Gerrans, El Dorado Hills, CA (US)

(73) Assignee: Sanovas, Inc., Sausalito, CA (US)

( * ) Notice: Subject to any disclaimer, the term of this patent is extended or adjusted under 35 U.S.C. 154(b) by 1220 days.

(21) Appl. No.: 12/912,499

(22) Filed: Oct. 26, 2010

(65) Prior Publication Data
US 2011/0270184 A1    Nov. 3, 2011

Related U.S. Application Data

(60) Provisional application No. 61/329,021, filed on Apr. 28, 2010.

(51) Int. Cl.
*A61M 5/00*    (2006.01)
*A61M 25/00*   (2006.01)
(Continued)

(52) U.S. Cl.
CPC ......... *A61M 25/0084* (2013.01); *A61B 18/24* (2013.01); *A61B 18/1492* (2013.01);
(Continued)

(58) Field of Classification Search
CPC .... A61M 25/0084; A61M 5/142; A61M 5/30; A61M 2005/1726; A61M 2025/0085; A61M 5/3295; A61M 2025/0087
(Continued)

(56) References Cited

U.S. PATENT DOCUMENTS 4,007,739 A * 2/1977 Bron et al. .................. 604/144
5,423,805 A * 6/1995 Brucker ................ A61B 18/24
                                                          606/15
(Continued)

FOREIGN PATENT DOCUMENTS

WO        9921609 A1    5/1999
WO        0147586 A1    7/2001
WO     2010051369 A1    5/2010

OTHER PUBLICATIONS

European Search Report; Application No. EP 11 30 5508; Issued: Aug. 25, 2011; 9 pages.

*Primary Examiner* — Matthew F Desanto
(74) *Attorney, Agent, or Firm* — St. Onge Steward Johnston & Reens LLC

(57) ABSTRACT

A delivery probe for delivering a therapeutic agent to tissue is described including at least one delivery capsule for accommodating the agent, at least one delivery device in fluid communication with the capsule, an actuation mechanism for moving the capsule between an activated position and an inactivated position by providing at least one of a fluid and a vacuum, and a delivery mechanism for forcing the agent out of the capsule. A method of delivering a therapeutic agent to tissue is also described including providing a catheter with a delivery probe at a distal end, positioning the delivery probe next to the tissue, supplying fluid to an actuation chamber to position the probe into an activated position, supplying fluid to a delivery chamber to force the agent out of the probe, and establishing a vacuum in the actuation chamber to position the probe into an inactivated position.

28 Claims, 13 Drawing Sheets

(51) Int. Cl.
*A61B 18/24* (2006.01)
*A61B 18/14* (2006.01)
*A61M 5/142* (2006.01)
*A61M 5/172* (2006.01)

(52) U.S. Cl.
CPC ..... *A61M 5/142* (2013.01); *A61M 2005/1726* (2013.01); *A61M 2025/0085* (2013.01)

(58) Field of Classification Search
USPC .... 604/140–151, 93.01, 264, 181, 187, 212, 604/218, 221
See application file for complete search history.

(56) References Cited

U.S. PATENT DOCUMENTS

| | | |
|---|---|---|
| 6,004,295 A | 12/1999 | Langer et al. |
| 6,309,370 B1 | 10/2001 | Haim et al. |
| 6,569,144 B2* | 5/2003 | Altman ........................ 604/507 |
| 6,689,103 B1 | 2/2004 | Palasis |
| 7,141,041 B2* | 11/2006 | Seward ............. A61M 25/0069 604/164.12 |
| 7,429,258 B2* | 9/2008 | Angel et al. .................. 604/173 |
| 7,637,891 B2* | 12/2009 | Wall .............................. 604/131 |
| 7,678,081 B2* | 3/2010 | Whiting et al. ......... 604/164.13 |
| 7,686,788 B2 | 3/2010 | Freyman et al. |
| 2004/0260234 A1* | 12/2004 | Srinivasan .............. A61M 5/30 604/66 |
| 2006/0200083 A1 | 9/2006 | Freyman et al. |
| 2007/0038181 A1 | 2/2007 | Melamud et al. |
| 2007/0249999 A1 | 10/2007 | Sklar et al. |
| 2010/0121270 A1 | 5/2010 | Gunday et al. |

\* cited by examiner

PRESSURE/VACUUM ACTUATED CATHETER DRUG DELIVERY PROBE

CROSS-REFERENCE TO RELATED APPLICATIONS

This application claims the benefit of the filing date of the U.S. Provisional application No. 61/329,021, filed on Apr. 28, 2010, which is incorporated by reference herein.

FIELD OF THE INVENTION

The present invention generally relates to systems and methods of delivering drugs. More specifically, the present invention relates to the delivery of diagnostic and therapeutic agents to specific locations in the body via pressurized a fluid and/or vacuum actuated catheter drug delivery probe.

BACKGROUND OF THE INVENTION

In treating diseases of various body organs, it is necessary to deliver drugs or other agents to the organs at specified locations. Most common routes of drug delivery include a non-invasive peroral (through the mouth), topical (skin), transmucosal (nasal, buccal/sublingual, vaginal, ocular and rectal) and inhalation routes. However, many therapeutic agents, such as peptide and protein, antibody, vaccine and gene based drugs, in general may not be delivered using these routes because they might be susceptible to enzymatic degradation or cannot be absorbed into the systemic circulation efficiently due to molecular size and charge issues, and thus, will not be therapeutically effective. For this reason, many such drugs have to be delivered by injection.

Often, it is necessary to deliver medicinal or therapeutic substances to remote and tortuous blood vessels and other lumens within body organs, such as lungs. It is also important to be able to deliver defined doses of therapeutic and diagnostic substances because such substances are often very expensive or are capable of causing serious harm if delivered in excess. Several devices have been proposed for a targeted delivery of drugs to internal bodily cavities.

For example, U.S. Pat. No. 6,309,370 to Haim et al. describes an apparatus for intracardic drug administration, including a catheter which is inserted into a chamber of the heart. The catheter includes a drug delivery device having a needle positioned within the catheter's distal end and a drug dispenser connected to the needle via a duct. The drug delivery device further includes a displacement mechanism, preferably a hydraulic piston, which drives the needle distally out of the distal end of the catheter to administer the drug.

U.S. Patent Publication No. 2007/0038181 to Melamud et al. describes a device for delivering a substance to organs, particularly the bladder. The device includes a delivery tube, a chamber to be filled with the substance to be delivered, a plurality of needles, and a plunger coupled to a handle movable relative to the tube to deliver the substance through the needles.

U.S. Pat. No. 6,004,295 to Langer et al. describes a catheter assembly for injecting therapeutic liquids into a patient's myocardium. The catheter assembly comprises an elongated catheter, a reservoir for therapeutic liquid positioned at a distal end of the catheter, one or more injection needles protruding from the distal end of the catheter in fluid communication with the reservoir and a hydraulic syringe for delivering the therapeutic liquid from the reservoir through the needles.

However, the known drug delivery systems such as those described above suffer from a number of disadvantages and shortcomings. For example, the prior art delivery systems are usually specifically adapted for delivering drugs to particular body organs, and therefore are unsuitable for use on a variety of internal organs and tissues. Additionally, the prior art devices are incapable of delivering therapeutic or medicinal fluids in precise quantities. Furthermore, known delivery devices are complex, bulky and difficult to introduce into remote locations within a patient's body, e.g. lungs.

What is desired, therefore, is a drug delivery system and method that overcomes the problems of known prior art drug delivery devices. It is also desired to provide a drug delivery device that allows for accurate delivery of medicinal and therapeutic substances to remote and not easily accessible locations in a patient's body. It is further desired to provide a device capable of delivering precise quantities of a drug to a desired internal organ or tissue, as well as enabling the application of various electrodes and/or probes for measuring certain tissue characteristics, such as oxygen concentration in the tissue. It is also desired to provide a delivery device that is efficient and that can be manufactured at a relatively low cost.

SUMMARY OF THE INVENTION

It is, therefore, an object of the present invention to provide a new and improved system and method for delivering medicinal diagnostics and therapies to specific locations of the body that overcome the above discussed shortcomings of known delivery methods and systems.

In order to overcome the deficiencies of the prior art and to achieve at least some of the objects and advantages listed, a delivery probe for delivering a therapeutic agent to tissue is provided comprising a housing, at least one delivery capsule for accommodating the agent to be delivered movably arranged in a housing, an actuation mechanism for moving the capsule between an activated position and an inactivated position by providing at least one of a fluid and a vacuum, at least one delivery device in fluid communication with the capsule, and a delivery mechanism for forcing the agent out of the capsule via the delivery device.

In some embodiments, the at least one delivery capsule includes a first chamber for accommodating therapeutic agent to be delivered and a second chamber fluidly isolated from the first chamber by a piston slidably disposed in the capsule. In some of these embodiments, the at least one delivery device is in fluid communication with the first chamber. In certain embodiments, the at least one delivery device is a needle. Similarly, in certain embodiments at least one wall of the housing comprises a membrane pierceable by the at least one delivery device.

In certain embodiments, the actuation mechanism includes an actuation chamber provided in the housing in fluid communication with the second chamber. In some of these embodiments, the actuation mechanism is an inflatable balloon.

In some embodiments, the delivery mechanism includes a delivery chamber fluidly isolated from the actuation mechanism and the capsule. In some of these embodiments, the piston is movable by supplying fluid to the delivery chamber.

In some embodiments, fluid is supplied by a fluid source connected to at least one of the actuation and delivery mechanisms. In some of these embodiments, the fluid source further includes a vacuum source. In certain embodiments, the fluid source is a pump. In certain advantageous embodiments, the pump is an electro-pneumatic pump. In certain embodiments, the pump includes a processor that controls the supply of fluid based on at least one predetermined parameter.

In certain embodiments, the at least one delivery device is enclosed by the housing when in the inactivated position.

In some cases, the at least one delivery device extends beyond a distal end of the housing when in the activated position. The at least one delivery device may also extend beyond at least one sidewall of the housing when in the activated position.

In some embodiments, the delivery probe further includes at least one imaging marker. In certain embodiments, the delivery probe may further include at least one connector for connection to a catheter. In some advantageous embodiments, the at least one capsule comprises a first delivery capsule and a second delivery capsule, and the actuation mechanism includes an actuation chamber between the first and the second delivery capsules.

In certain advantageous embodiments, the at least one delivery device includes at least one sensor for measuring at least one parameter associated with the tissue. In additional advantageous embodiments, the actuation mechanism includes at least one piezo-electric element. In yet further embodiments, the housing includes an expansion apparatus affixed to an outer wall of the housing.

The invention also comprises a delivery probe for delivering a therapeutic agent to tissue including a housing, at least one delivery capsule movably arranged within the housing and having a first chamber for containing the agent to be delivered and a second chamber sealed from the first chamber by a piston slidably disposed in the capsule, at least one delivery device in fluid communication with the first chamber, a delivery chamber provided in the housing in fluid communication with the second chamber, and an actuation chamber fluidly isolated from the delivery chamber. The at least one delivery device moves between an activated position and an inactivated position in response to the supply of fluid or vacuum in the actuation chamber. The piston moves from a first position to a second position in response to the supply of fluid to the delivery chamber.

The invention further comprises a catheter assembly for delivering a therapeutic agent to tissue including a shaft having at least one inner lumen and a delivery probe positioned at a distal end of the shaft. The delivery probe includes at least one delivery capsule movably arranged in a housing, at least one delivery device in fluid communication with the capsule, an actuation mechanism for moving the capsule between an activated position and an inactivated position by providing at least one of a fluid and a vacuum, and a delivery mechanism for delivering the agent to the tissue.

In some embodiments, the shaft has a first lumen in fluid communication with the actuation chamber and a second lumen in fluid communication with the delivery chamber.

In certain embodiments, the catheter assembly further includes at least one guidewire disposed in the shaft. In some embodiments, the catheter assembly also includes an imaging device positioned at the distal end of the shaft for viewing the tissue. The catheter assembly may further include a control device positioned at a proximal end of the shaft and connected to the delivery probe for actuation of the probe.

A method of delivering a therapeutic agent to tissue is also described, including the steps of providing a catheter having a delivery probe at a distal end of the catheter and containing the agent to be delivered, positioning the delivery probe next to the tissue, supplying a fluid to an actuation chamber provided in the delivery probe to position the probe into an activated position, supplying a fluid to a delivery chamber to force the therapeutic agent out of the probe and into the tissue, and providing a vacuum to the actuation chamber to position the delivery probe into an inactivated position.

In some embodiments, the step of positioning the probe into the activated position includes extending at least one delivery device beyond an outer surface of the probe such that the at least one delivery device extends into the tissue. In certain embodiments, the step of positioning the probe into the inactivated position comprises retracting the at least one delivery device into the probe.

In certain advantageous embodiments, the steps of providing fluid and vacuum are performed by a pump connected to the probe. In some cases, the steps of providing fluid and vacuum are controlled via a control device provided at a proximal end of said catheter.

Other objects of the invention and its particular features and advantages will become more apparent from consideration of the following drawings and accompanying detailed description.

DETAILED DESCRIPTION OF THE INVENTION

Figure 1A:
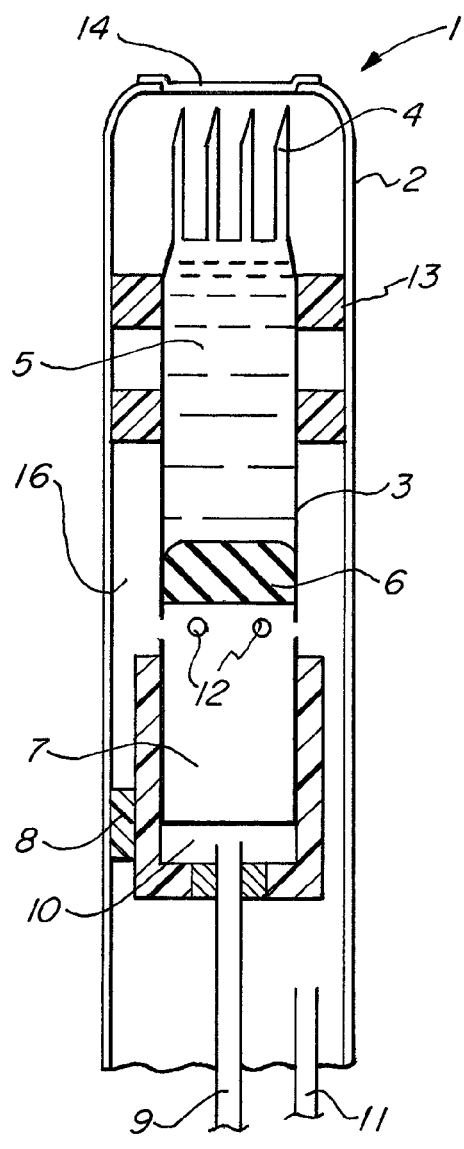
FIG. 1A is a cross-sectional view of a delivery probe in accordance with the invention.

The basic components of one embodiment of a delivery probe for delivering a therapeutic agent to tissue in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The delivery probe of the present invention may be used to deliver drugs, radiation therapies, chemo therapies, pharmacologic medicines, therapeutic agents, immuno-therapies, biologic materials, biologic markers, radio opaque contrasts, diagnostic agents and related technologies to specific cellular locations within and adjacent to bodily cavities. The delivery probe of the present invention may also be used to deliver probes and/or electrodes to the tissue to measure and quantify certain tissue characteristics, such as oxygen content. For example, the delivery probe may be used to deliver substances to tubular structures, tumor tissues, lumens, pleural cavities and other spaces within the body such as airways, vessels, organs, bones and joints necessitating delivery of a diagnostic or therapeutic agent to a specific location within the body for diagnostic examination and therapeutic treatment.

The delivery probe of the present invention may be used with guide wires, steerable catheters, imaging devices, catheter devices, surgical instruments and tools, operative devices, implants and related medical diagnostic and treatment systems. The delivery probe may be removably attached to the above devices and may be disposed of after use. The delivery probe can be introduced into the body through a natural orifice or through an incision. In some embodiments, the delivery probe is deployed into a patient's body via a steerable catheter having one or more inner lumens or the working channel of a flexible or rigid endoscope. In an advantageous embodiment, the delivery probe is used with a resector balloon system described in U.S. patent application Ser. No. 12/269,495, the disclosure of which is incorporated by reference herein in its entirety.

Figure 1B:
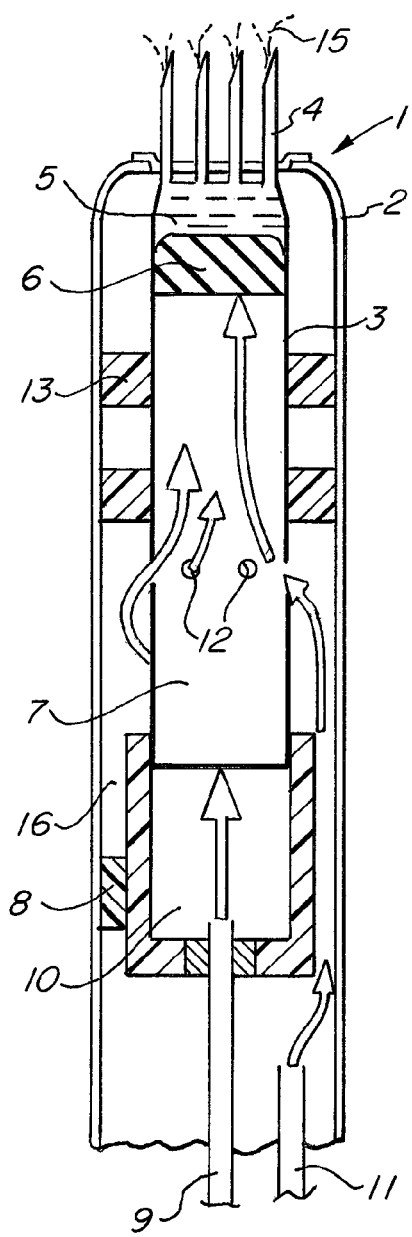
FIG. 1B is a cross-sectional view of the delivery probe of FIG. 1A, shown in an activated position.

FIGS. 1A and 1B illustrate one exemplary embodiment of the delivery probe for delivering a therapeutic agent to tissue according to the present invention. The delivery probe (1) includes an outer housing (2) that houses various components of the probe. The outer housing (2) may be made out of any suitable material, such as stainless steel or polyethylene, and may have a variety of different shapes depending on a particular application. In the embodiment depicted in FIGS. 1A and 1B, the housing (2) has an elongate cylindrical shape. An outer diameter of the housing (2) is preferably the smaller than an inner diameter of a catheter and/or endoscope working channel to facilitate the insertion of the delivery probe into a patient's body.

The housing (2) houses a delivery capsule (3) containing a therapeutic agent (15) to be delivered. The delivery capsule (3) can be made in a variety of suitable sizes and shapes. In some embodiments, the capsule (3) is pre-filled during manufacturing processes. In other embodiments, the delivery capsule (3) is filled in the operating room with a filling apparatus. In yet other embodiments, the therapeutic substance is provided via a separate lumen provided in a catheter shaft and connected to the delivery capsule (3).

The delivery capsule (3) is movably arranged in the housing (2) and is comprised of a plurality of sections. The distal tip of the capsule (3) contains at least one delivery device (4) that, when extended, penetrates the tissue and delivers the therapeutic agent (15) that is contained in the delivery capsule (3). In the preferred embodiment of the present invention, the delivery device (4) comprises at least one needle disposed at the distal end of the delivery capsule (3). It should be noted that any number of needles may be provided in accordance with the present invention. Additionally, the needle(s) may be arranged in any suitable configuration, e.g. in a circle, in a vertical or horizontal line, in several vertical/horizontal lines, etc., and can be of any length suitable for a particular application.

The needles (4) can be extended out as desired, to particular lengths or in particular combinations/sequences, in order to meet the needs of the particular procedure, which may be based on the type of tissue or the desired depth and/or timing of injection of the drug. Additionally, the needles (4) may have holes on their sides (which may be located at different lengths along the length of the needles) for delivering the therapeutic agent (15) laterally and/or via a hole at the tip. While in some applications, the needles (4) puncture the targeted tissue, in other applications, the needles (4) do not enter the tissue, but instead, spray the surface of the tissue with the drug.

It should be noted that any other suitable drug delivery conduit or device can be used in place of the needles, depending on the requirements of the particular medical application for which the probe is being employed. In some embodiments, the delivery device is a material coated or soaked with the therapeutic agent to be delivered. In additional embodiments, the delivery device is a textured surface through which the therapeutic agent is topically delivered to the tissue.

In an advantageous embodiment, the delivery probe (1) further includes at least one sensor for measuring various characteristics of bodily tissue to facilitate precise and efficient delivery of the drug. For example, it may be desirable to measure oxygen concentration of tissue, such as cancerous tissue. Any type of suitable sensor can be used in accordance with the present invention. The sensors are positioned on or in proximity of the delivery device (4) or any other suitable location along the probe.

In some advantageous embodiments, the delivery device (4) may include at least one conductive probe, e.g. an electrode or an optical device, such as an optical fiber, capable of conducting infra red (IR) light, near infra red (NIR) light, ultra violet (UV) light and/or ultrasound waves, to assist in diagnosis and/or treatment of specific medical conditions.

In further advantageous embodiments, the delivery device (4) can supply additional media to tissue, e.g. medical grade oxygen. For example, tumor tissues are known to be hypoxic (having low concentrations of oxygen), and do not respond well to radiation treatment. Therefore, measuring the oxygen pressure and delivering oxygen to increase the oxygen concentration, coupled with a synchronized triggering of the radiation treatment, is important in treatment of the tumor tissues.

The rounded distal tip of the outer housing (2) includes a semi-soft membrane (14) that seals the housing (2) and that can be punctured by the needles (4) located at the distal tip of the delivery capsule (3). The membrane (14) can be made out of any material suitable for medical applications and that can be easily punctured by the needles (4).

The delivery capsule (3) also includes a first chamber (5) for containing the therapeutic agent (15) to be delivered. The first chamber (5) is in fluid communication with the needles (4). The delivery capsule (3) further includes a second chamber (7) fluidly isolated from the first chamber (5) by a piston (6) slidably disposed in the delivery capsule. The piston (6) seals the therapeutic agent in the first chamber (5) and moves forward as the second chamber (7) behind it is filled with the pressurized fluid (e.g., air), which in turn causes the agent in the chamber (5) to move out through the needles (4) and into the targeted tissue.

The outer housing (2) includes a delivery chamber (16) surrounding the delivery capsule (3). The delivery chamber is in fluid communication with the second chamber (7) of the delivery capsule (3) such that the pressurized fluid used to actuate the piston (6) is supplied from the delivery chamber (16) to the second chamber (7). In some advantageous embodiments, the pressurized fluid may enter the second chamber (7) from the delivery chamber (16) through air access holes (12) provided in walls of the second chamber. The pressurized fluid, supplied to the delivery chamber (16) via a first lumen (11) of the probe catheter, enters the second chamber (7) behind the piston through the openings (12) and eventually pushes the piston toward the drug filled chamber (5).

The outer housing (2) further includes an actuation chamber (10) located adjacent to the proximal end of the capsule (3) and fluidly isolated from the capsule (3) and the delivery chamber (16). The pressurized fluid used to actuate the delivery capsule (3) is supplied to the actuation chamber (10) through a second lumen (9) of the probe catheter. As the pressurized fluid enters the actuation chamber (10), it pushes the delivery capsule (3) forward, causing the needles (4) to extend beyond the distal end of the outer housing (2) by puncturing the membrane (14) and to penetrate the targeted tissue. After the therapeutic agent (15) is delivered to the tissue, a vacuum (e.g. negative pressure) is applied to the actuation chamber (10) to cause the delivery capsule (3) to retract back into the probe housing (2).

The delivery probe (1) is provided with guides (13) and (8) positioned on an inside surface of the outer housing (2). The guides hold the drug capsule (3) in place and allow the drug capsule to move forward, deploying the needles to the target site, or to move backward, retracting the needles from the target site.

FIG. 1B illustrates the delivery probe (1) in an activated position. As shown in this figure, the pressurized fluid enters the actuation chamber through the lumen (9) causing the delivery capsule (3) to move toward the distal end of the housing (2), which in turn causes the needles (4) to pierce the membrane (14) and to penetrate the surrounding tissue. The pressurized fluid is then supplied to the delivery chamber (16) through the lumen (11). The fluid enters the second chamber (7) via the openings (12) and causes the piston (6) to move toward the distal end of the capsule, thereby forcing the therapeutic agent (15) out of the needles (4) and into the tissue.

Figures 2A, 2B, 2C:
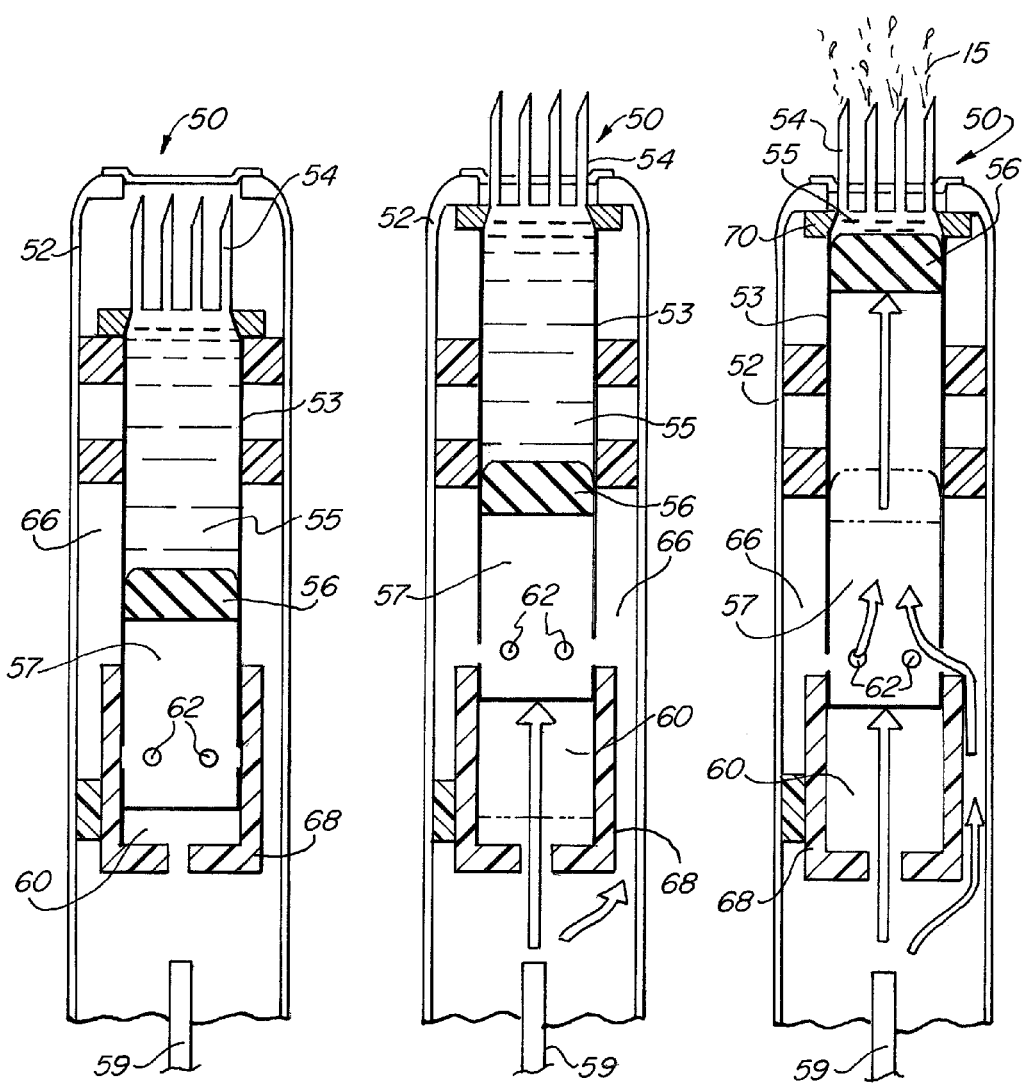
FIGS. 2A-2C are cross-sectional views of an alternative configuration of the delivery probe of FIG. 1A.

FIGS. 2A-2C illustrate another embodiment of the delivery probe (1) in accordance with the present invention. In this embodiment, the delivery probe (50) is connected to a single lumen (59) that supplies fluid to the delivery probe. The delivery probe (50) includes a delivery capsule (53) with a first chamber (55) and a second chamber (57), fluidly isolated from the first chamber (55) by a slidable piston (56). The delivery probe (50) further includes a delivery device (54) in fluid communication with the first chamber (55), a delivery chamber (66) surrounding the delivery capsule (53) and in fluid communication with the second chamber (57) through openings (62), and an actuation chamber (60) fluidly isolated from the capsule (53) and the delivery chamber (66).

As shown in FIG. 2A, when the delivery probe (50) is in inactivated position, the delivery capsule (53) is housed within a sleeve (68) such that the openings (62) are covered by the sleeve (68) and therefore the delivery chamber (66) is fluidly isolated from the second chamber (57) of the delivery capsule. As the pressurized fluid enters the chamber (66) through the lumen (59), it also enters the actuation chamber (60) and begins to move the delivery capsule (53) towards the distal end of the delivery probe. The delivery capsule continues to move until stoppers (70) provided on the distal end of the capsule contact the distal end of the housing, as shown in FIG. 2B. In this position, the openings (62) become exposed to the delivery chamber (66) and the pressurized air begins to enter the second chamber (57) though the openings (62), which in turn causes the piston (56) to move toward the drug filled chamber (55).

As the piston (56) is pushed forward, it forces the therapeutic agent (15) out of the drug filled chamber (55) through the delivery device (54) and into tissue, as shown in FIG. 2C. After the necessary amount of the therapeutic agent is delivered to the tissue, a vacuum is applied to the actuation chamber (60) through the lumen (59) to cause the delivery capsule (53) to retract back into the probe housing (52).

Figure 3:
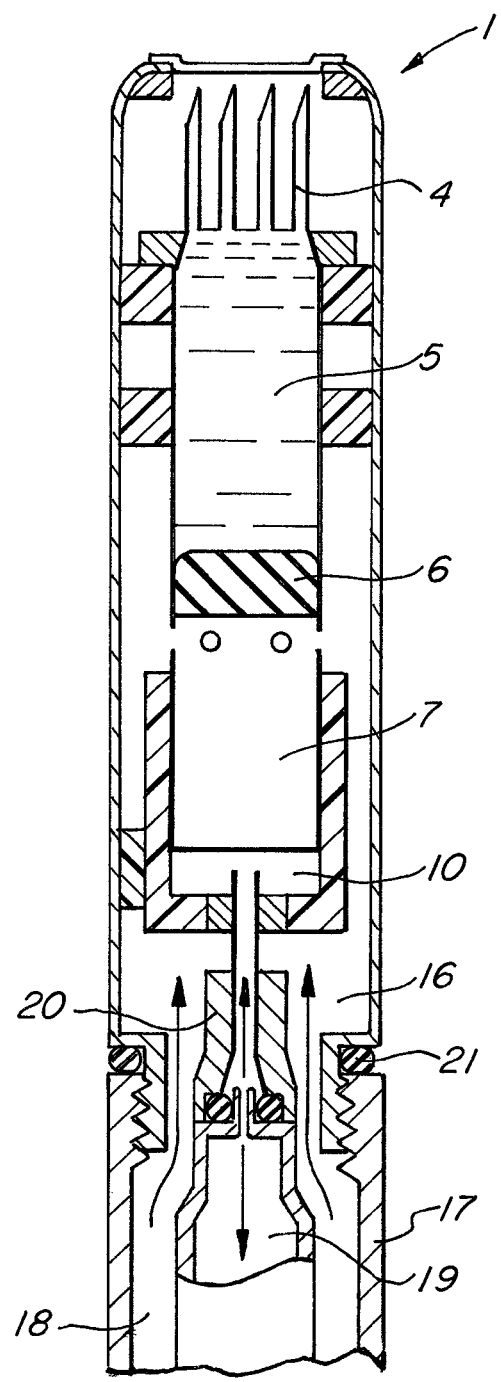
FIG. 3 is a partially cross-sectional view of the delivery probe of FIG. 1A, showing connections to a catheter.

As shown in FIG. 3, the delivery probe (1) also includes a connection mechanism such that the attachment of the delivery probe to a distal end of a catheter is made in a fast and reliable manner. With the connection mechanism, a pre-filled drug delivery probe can be provided by the drug manufacturers, which can then be easily connected to any type of a catheter or endoscope. Additionally, the connection mechanism provides an easy way to connect the probe to the drug filling apparatus in cases where the probe is to be filled with the drug in the operating room. Any suitable mechanism may be employed, such as, for example, a threaded connection, a screw-in connection, a snap-in connection, etc.

The delivery probe (1) may be deployed to an operative site via, for example, a suitable guiding catheter, a working channel of a rigid or flexible endoscope, or the resector balloon system described in U.S. patent application Ser. No. 12/269,495. FIG. 3 depicts the delivery probe (1) that is constructed at a distal end of a two-lumen catheter. It is noted, however, that a one-lumen catheter, as shown in FIGS. 2A-2C may be used as well without departing from the spirit of the present invention.

Referring to FIG. 3, the catheter has a shaft (17) with an inner lumen (19) for providing a pressurized fluid/vacuum to the actuation chamber (10) of the probe for actuating the delivery capsule (3), and an outer lumen (18) for providing the pressurized fluid to the delivery chamber (16) for pushing the piston (6) toward the drug containing chamber (5) for delivering the drug. The inner lumen (19) of the catheter shaft (17) is provided with a nozzle (20). When the shaft (17) is connected to the probe (1), the nozzle (20) is coupled with the lumen (9) of the probe, such that an airtight connection is provided between the probe (1) and the catheter, which delivers pressurized fluid/vacuum that deploys and retracts the delivery capsule. The proximal end of the probe (1) can be provided with O-rings (21) that facilitate an airtight coupling between the outer lumen (18) of the catheter shaft (17) and the delivery chamber (16) of the probe (1), as the outer catheter lumen delivers pressurized fluid to push the piston (6) forward and deliver the drug. It should be understood that any other kind of connection mechanism can be used to connect the probe (1) to the catheter in accordance with the invention.

In should be noted that, in advantageous embodiments wherein the delivery device (4) is provided with electrodes and/or optical fibers, one or more lumens in the catheter will contain conductors.

Figure 4:
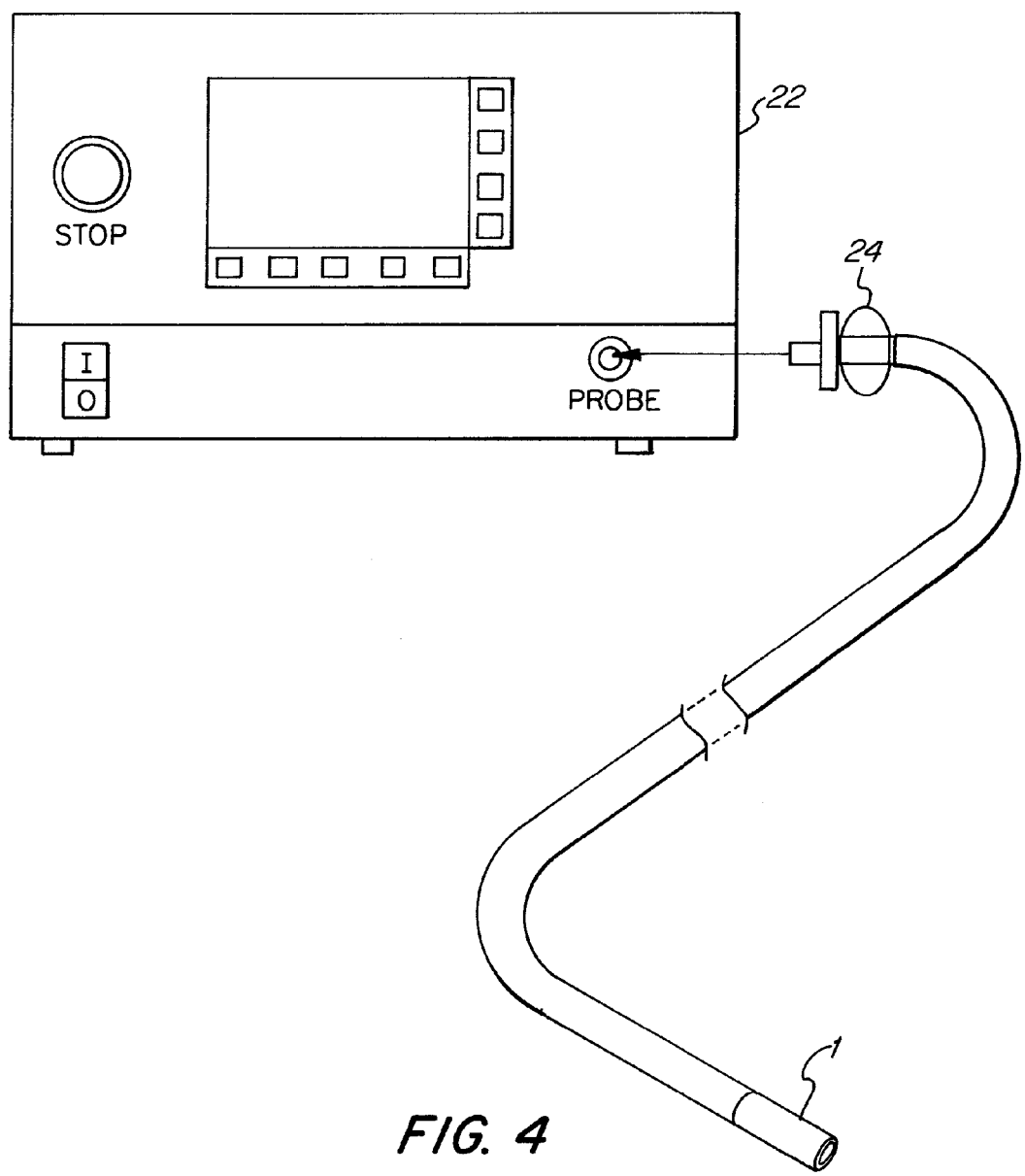
FIG. 4 is a partially schematic view of a catheter assembly with a pump in accordance with the invention.

The pressurized fluid and/or vacuum may be provided to the delivery chamber (16) and the actuation chamber (10) via any suitable fluid/vacuum source. In a preferred embodiment shown in FIG. 4, the delivery probe (1) is connected to a pump (22), which supplies a fluid, such as a gas, liquid, or mixture thereof to the delivery probe (1). The delivery probe (1) is connected to the pump (22) via any suitable connector (24). In some advantageous embodiments, the connector (24) carries electric probes used to measure various tissue characteristics, as described above.

The pump (22) preferably includes a compressor and a fluid tank. The fluid pressure in the tank may be continuously monitored by a microcontroller provided with the pump (22). Any suitable known type of microcontroller may be used in accordance with the present invention. The microcontroller initiates the compressor to operate via an electrical signal output. In another variation of the pump (22), the pressurized fluid may be instead provided from an external source, such as a gas tank or the operating room walls commonly found in an operating room. A vacuum source is also included in the pump (22). The vacuum source is turned on and off by the microcontroller via an electrical output signal. In advantageous embodiments, the pump (22)

further includes an interface connection to external devices for measuring tissue characteristics, synchronization and triggering of other therapeutic and/or diagnostic devices.

The delivery probe (1) can be provided in many different shapes and can be used with various additional devices. In some embodiments, it is coupled with an imaging system (not shown), e.g. a fiber optic image bundle, for imaging of the surrounding area during the introduction of the drug delivery probe into the patient's body. Two separate bundles, one for illumination and the other for imaging can also be used. It should be noted that other sources of illumination and/or imaging may also be employed. It should also be noted that the image sensor and/or illumination source (such as high power LEDs) can be located at the tip of the probe, eliminating the need for a coherent imaging fiber bundle, thus increasing image quality and reducing cost.

In an advantageous embodiment, the proximal end of the delivery probe (1) includes a hand piece (not shown) for actuation of the probe by a physician. The probe (1) is actuated by interchangeably applying pressurized fluid (e.g., air) and a vacuum (e.g. below atmospheric pressure) to cause the delivery capsule (3) to move forward, deploying the needles (4) and releasing the therapeutic agent (15), or to move back, retracting the needles (4) once the agent is delivered to a desired site. This procedure can be repeated as many times as required by the physician. Likewise, the actuation of the probe (5) may be controlled via other means, such as voice control.

Figure 5A:
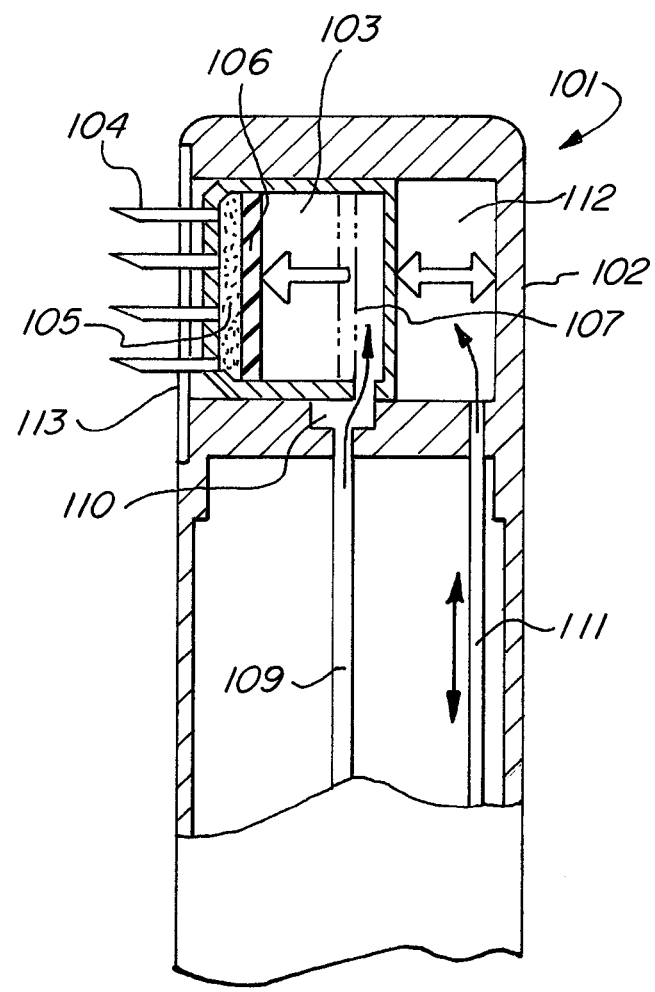
FIGS. 5A-9B illustrate cross-sectional, partially schematic views of various configurations of the delivery probe of FIG. 1A.
Figures 5B, 5C:
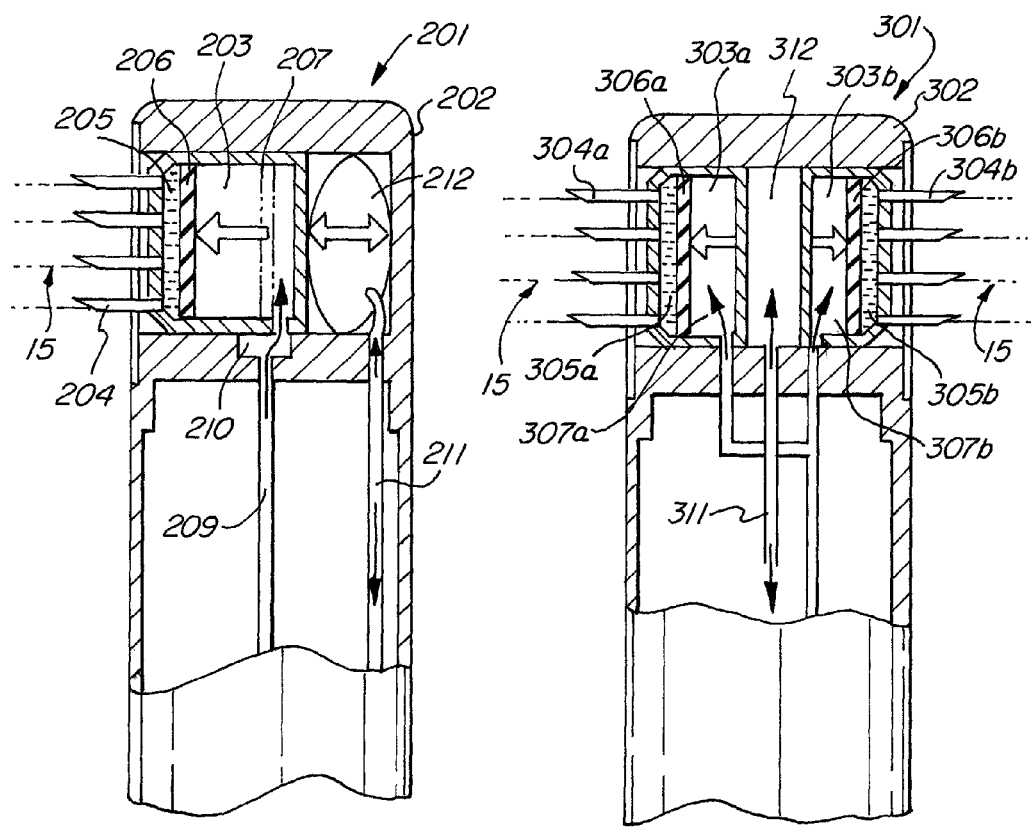

FIGS. 5A-5C illustrate several alternative embodiments of the delivery probe (1), which allow for directional and more targeted delivery of a therapeutic agent.

The embodiment of the delivery probe (101) depicted in FIG. 5A allows for a directional lateral delivery of the therapeutic agent to the tissue. The delivery probe (101) includes an outer housing (102) having an elongated cylindrical shape, although other shapes can be utilized in accordance with the present invention. The housing (102) houses a delivery capsule (103) slidably arranged in the housing and containing a therapeutic agent to be delivered. In this embodiment, the delivery capsule is arranged to slide in a direction perpendicular to a longitudinal axis of the probe (101), such that when the capsule (103) is an activated position, the delivery mechanism (104), e.g. a plurality of needles, extends beyond one of the sidewalls of the housing (102). The housing (102) has a pierceable membrane (113) provided in a sidewall adjacent to the delivery capsule (103), which is penetrated by the needles (104).

It should be noted that the needles may be arranged in any suitable configuration and can be of any length suitable for a particular application. Additionally, the needles may be positioned at different angles with respect to the outer housing wall to allow for more precise delivery of the therapeutic agent. Further, the needles may have different lengths, e.g. to accommodate a cylindrical housing.

The delivery capsule (103) includes a drug containing chamber (105) fluidly connected to the needles (104). The capsule also includes a chamber (107) fluidly isolated from the chamber (105) by a piston (106) slidably disposed in the delivery capsule.

The housing (102) includes a delivery chamber (110) directly connected to the chamber (107) within the delivery capsule (103), such that the pressurized fluid provided via a lumen (109) is supplied from the delivery chamber (110) to the chamber (107) to move the piston (106) laterally forcing the therapeutic agent into the tissue.

The housing (102) further includes an actuation chamber (112) located on the side of the housing opposite the delivery capsule (103) and fluidly isolated from the capsule and the delivery chamber (110). The pressurized fluid is supplied to the actuation chamber (112) through a second lumen (111), causing the capsule (103) to move laterally, thereby deploying the needles (104) into the tissue. After the therapeutic agent is delivered to the tissue, a vacuum is applied to the actuation chamber (112) to cause the delivery capsule (103) to retract back into the probe housing (102).

The embodiment of the delivery probe (101) shown in FIG. 5A is advantageous in that it allows for a targeted and precise delivery of the therapeutic agent to the tissue immediately adjacent to the sidewall of the probe housing. It should be noted that this embodiment can also be used with a single lumen catheter, as described above in connection with FIGS. 2A-2C, without departing from the spirit of the present invention. A combination of the embodiments shown in FIGS. 1A-1B or FIGS. 2A-2C and FIG. 5A can also be envisioned.

FIG. 5B illustrates another alternative embodiment of the delivery probe in accordance with the present invention. The delivery probe (201) includes a housing (202), and a delivery capsule (203) slidably disposed within the housing. The delivery capsule (203) includes a plurality of needles (204) positioned on one side of the capsule adjacent to the housing wall. The delivery capsule also includes a drug containing chamber (205) fluidly connected with the needles (204), and another chamber (207) fluidly isolated from the chamber (205) by a piston (206) slidably disposed in the delivery capsule.

The probe (201) further includes a delivery chamber (210) fluidly connected to the chamber (207) for supplying the pressurized fluid from the delivery chamber (210) to the chamber (207) via a lumen (209) to move the piston (206), thereby forcing the therapeutic agent (15) into the tissue. The housing (202) further includes an expansion apparatus (212) positioned adjacent to the delivery capsule (203) and fluidly isolated from the capsule and the delivery chamber (210). In certain embodiments, the expansion apparatus (212) is an inflatable balloon. However, other suitable expansion devices may be used in accordance with the present invention.

The pressurized fluid is supplied to the expansion apparatus (212) via a second lumen (211), causing the apparatus to expand/inflate, which in turn causes the capsule (203) to move toward the outer wall of the housing and to force the needles (204) into the target site, as shown in this figure. The expansion apparatus can be expanded slowly or rapidly, depending on the desired application. After the therapeutic agent is delivered to the site, a vacuum is applied to the expansion apparatus (212), which causes it to deflate, thereby retracting the delivery capsule with needles back into the probe housing (202). This embodiment can also be used with a single lumen catheter, as described above in connection with FIGS. 2A-2C, without departing from the spirit of the present invention.

FIG. 5C illustrates a further embodiment of the present invention that allows for a directional circumferential delivery of the therapeutic agent. In this embodiment, the delivery probe (301) includes two or more delivery capsules (303a, 303b), each positioned along the wall of the probe housing (302). Each capsule includes a plurality of needles (304a, 304b), a drug containing chamber (305a, 305b) in fluid communication with the needles, and a second chamber (307a, 307b) fluidly isolated from the first chamber by a piston (306a, 306b).

The delivery probe (301) further includes an actuation chamber (312) positioned in the central portion of the housing (302) between the delivery capsules (303a, 303b), and fluidly isolated from the capsules. A pressurized fluid is supplied to the actuation chamber (312) via a lumen (311), which causes lateral movement of the delivery capsules (303a, 303b) toward the sidewalls of the probe housing (302) and forces the needles (304a, 304b) into the surrounding airway or vessel walls. FIG. 5C shows the needles (304a, 304b) in an activated position. Once the desired amount of the drug is delivered, a vacuum is supplied to the actuation chamber (312), which causes the needles (304a, 304b) to pull out of the tissue and to retract back inside the housing (302).

It should be understood that a single lumen catheter, as described above in connection with FIGS. 2A-2C, can also be used with this embodiment of the delivery probe without departing from the spirit of the present invention.

Figure 6:
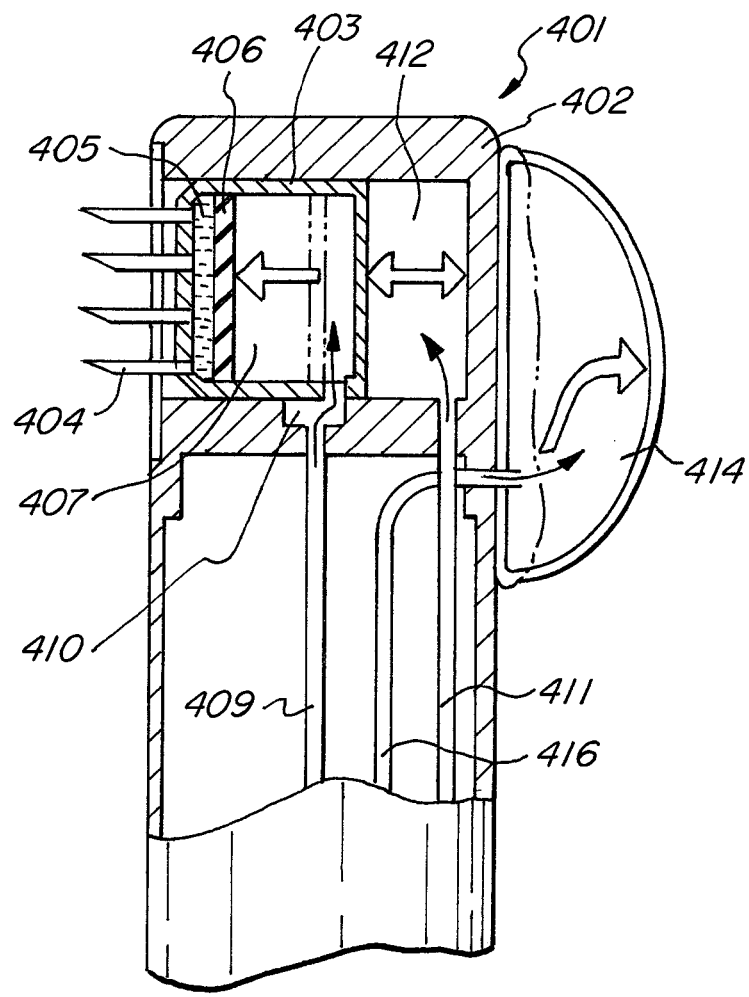

FIG. 6 illustrates yet another possible embodiment of the delivery probe in accordance with the present invention. This embodiment is similar to the one shown in FIG. 5A, and includes a delivery capsule (403) positioned inside an outer housing (402) and having a first chamber (405) and a second chamber (407), fluidly isolated from the first chamber (405) by a slidable piston (406). The delivery probe (401) further includes a delivery device (404) in fluid communication with the first chamber (405), a delivery chamber (410) in fluid communication with the second chamber (407), and an actuation chamber (412) fluidly isolated from the capsule (403) and the delivery chamber (410).

In this embodiment, the delivery probe (401) further includes an expansion device (414) affixed to an outer surface of the housing (402) opposite of the delivery device (404). As shown in FIG. 6, the expandable device (414) is an inflatable balloon having a half-sphere shape. The pressurized fluid is supplied to the balloon (414) via a lumen (416) to inflate the balloon. Once the balloon (414) is inflated, is pushes against a bodily cavity wall, which causes the delivery device (404) to come in closer contact with the tissue. This is particularly advantageous when the delivery probe is used in larger bodily lumens, wherein the delivery device (404) is not long enough to reach the bodily cavity wall to deliver the therapeutic agent into it.

Figures 7A, 7B:
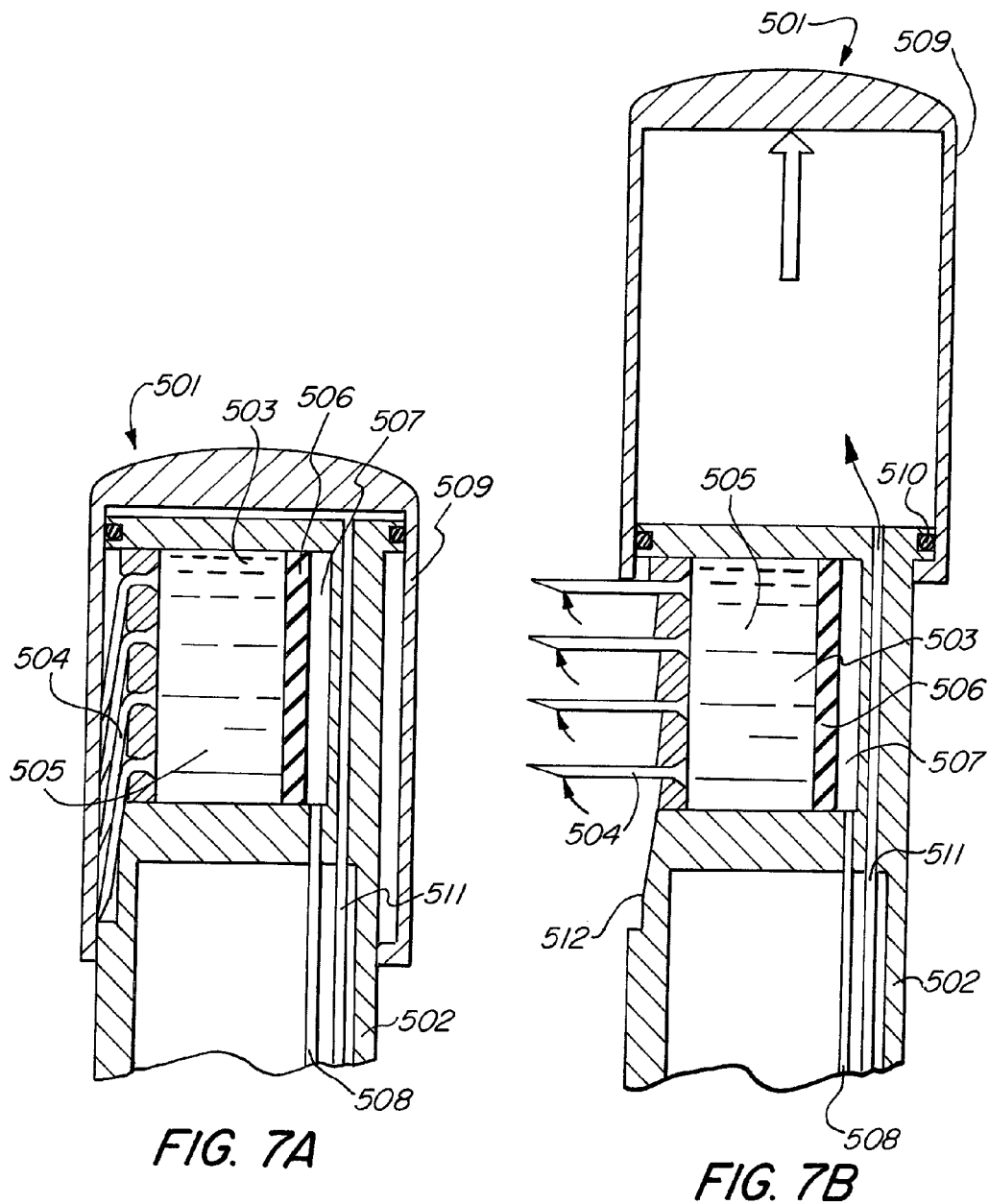
Figure 7C:
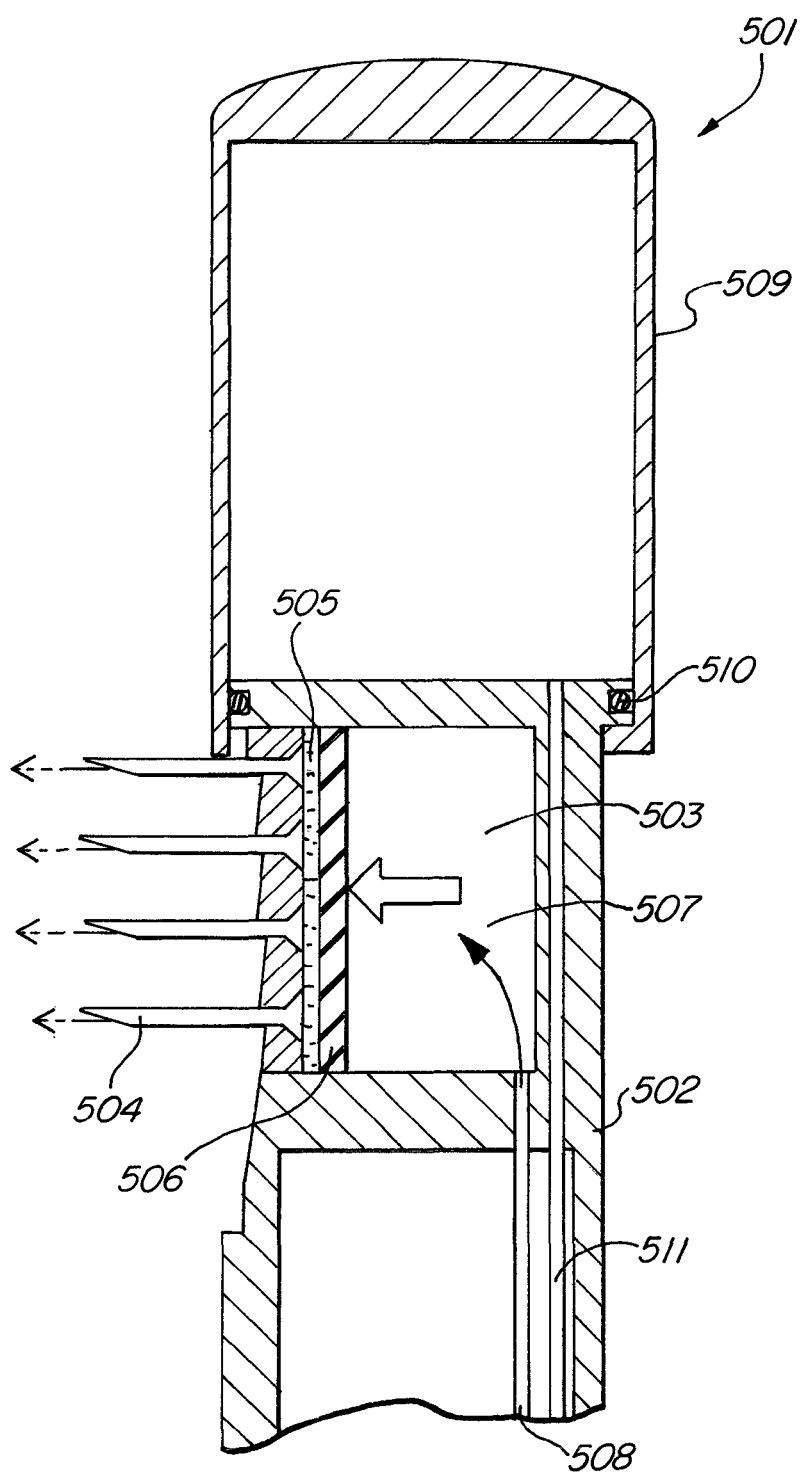

FIGS. 7A-7C illustrate another advantageous embodiment of the present invention. In this embodiment, the delivery probe (501) has a housing (502) with a delivery capsule (503) positioned therein and a delivery device (504), shown as a plurality of needles, in fluid communication with the capsule. The delivery capsule (503) has a first chamber (505) containing a therapeutic agent to be delivered and a second chamber (507) fluidly isolated from the first chamber (505) by a piston (506). The delivery probe (501) also includes a cap (509) slidably positioned at the distal end of the housing (502). The housing (502) has an elongated opening (512) to accommodate the needles (504).

When the delivery probe is in inactivated position, the needles (504) are folded into the housing (502) and are covered by the cap (509), as shown in FIG. 7A. Once the delivery probe is introduced into a bodily cavity, the pressurized fluid is supplied via a lumen (511) to push the cap (509) upward until it comes to an end position, shown in FIG. 7B. The housing (502) and the cap (509) are provided with stops (510) that prevent the cap (509) from completely disconnecting from the housing (502). As the cap (509) moves up, the needles (504) begin to splay outward, such that they protrude beyond the housing wall. The needles (504) are provided with a spring-loaded mechanism, or any other suitable mechanism, such that the needles (504) are connected in a sealed fashion to the chamber (505) via an elastic member which forces the needles outward as the cap (509) moves up. It should be noted that the cap can be removed only partially, such that the needles extend outward at any desirable angle, depending on a particular application.

Next, the pressurized fluid is delivered to the second chamber (507) via the lumen (508) to push the piston (506) toward the needles (504), thereby forcing the therapeutic agent out of the needles and into tissue, as shown in FIG. 7C. Once a desired amount of the therapeutic agent is delivered, a vacuum is applied through the lumen (511) causing the cap (509) to move back onto the housing (502), and thereby forcing the needles (504) into the inactivated position inside the housing. This embodiment is advantageous in that it allows for use of longer needles that may be required in larger bodily lumens.

Figure 8A:
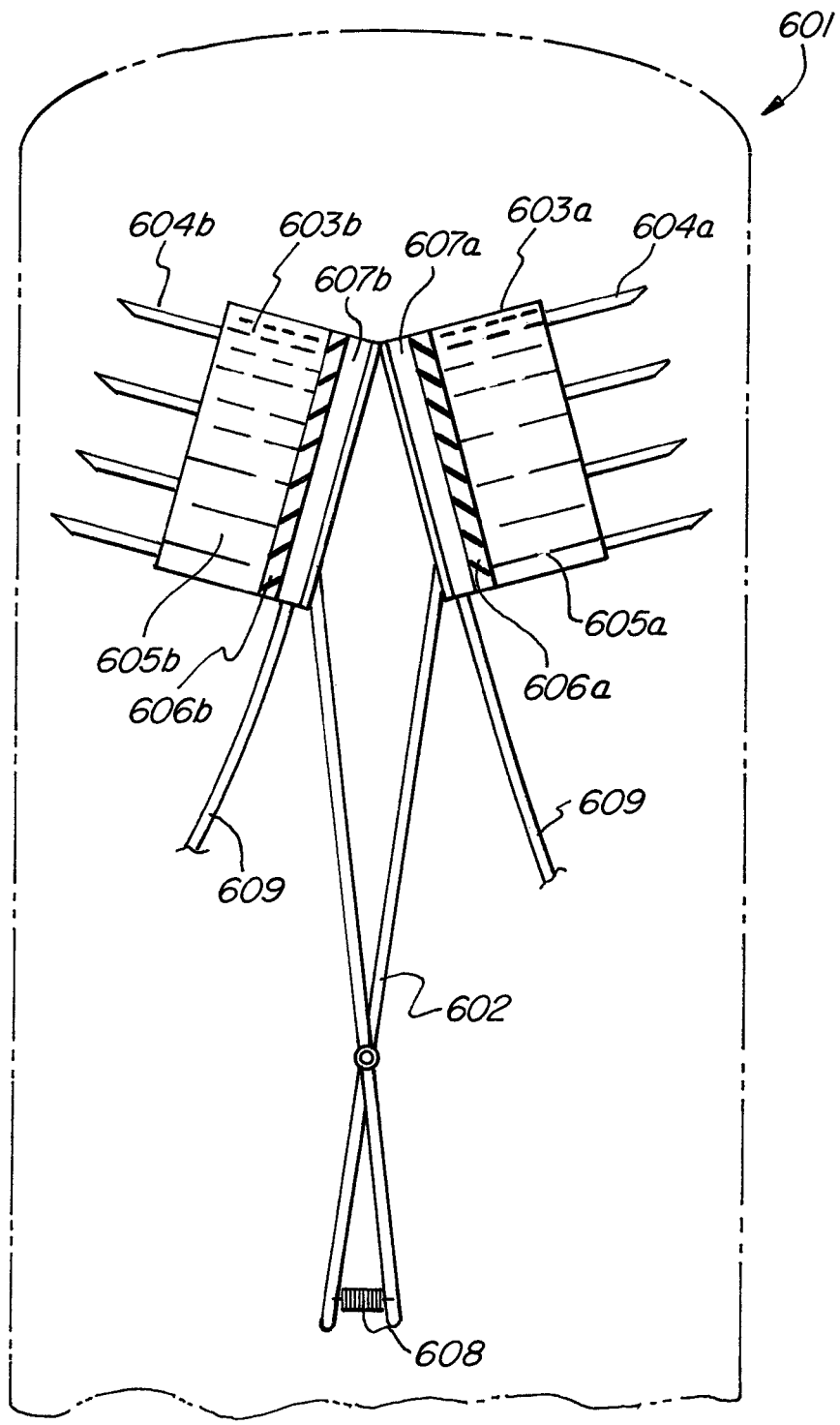
Figure 8B:
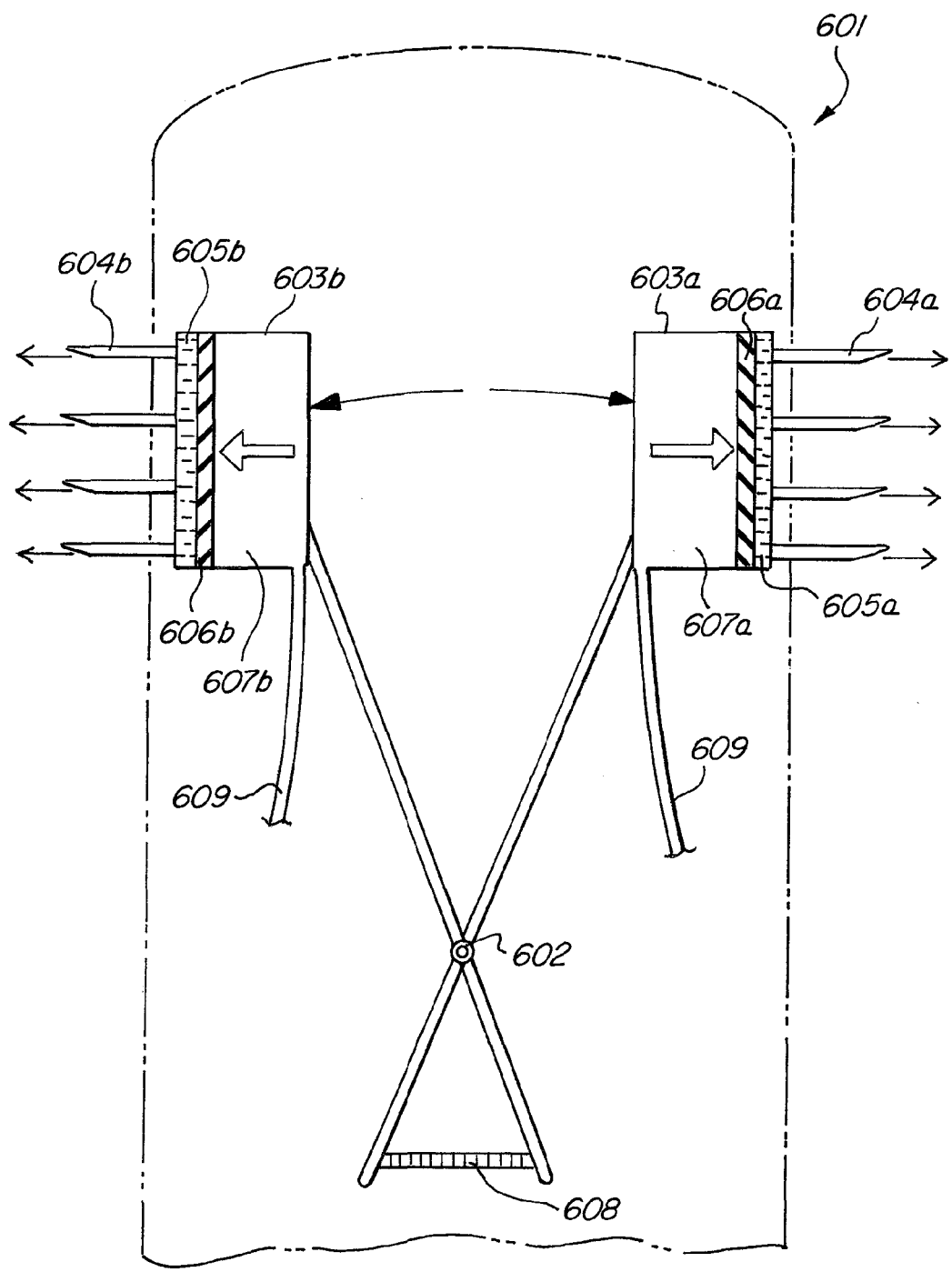

Another advantageous embodiment of the delivery probe (601) of the present invention is shown in FIGS. 8A and 8B. In this embodiment, the delivery probe (601) includes a housing, shown in phantom lines, and a scissor-like delivery mechanism (602) positioned within the housing. The delivery mechanism (602) includes two delivery capsules (603a, 603b) positioned on each upper arm of the scissor-like delivery mechanism (602). Each delivery capsule (603a, 603b) has a plurality of needles (604a, 604b), or any other suitable delivery mechanism, in fluid communication with a drug containing chamber (605a, 605b), and a second chamber (607a, 607b) fluidly isolated from the drug containing chamber (605a, 605b) by a slidable piston (606a, 606b). The delivery mechanism (602) further includes a piezo-electric stack (608), composed of piezo-electric crystals, positioned between and affixed to the lower arms of the delivery mechanism.

When the delivery probe is in inactivated position, as shown in FIG. 8A, the scissor-like delivery mechanism (602) is closed such that the delivery capsules (603a, 603b) with the needles (604a, 604b) are positioned inside the housing. To activate the delivery probe (601), energy is supplied to the piezo-electric stack (608), causing it to expand, which in turn causes the scissor-like delivery mechanism (602) to open, as shown in FIG. 8B. As the delivery mechanism (602) opens, the delivery capsules (603a, 603b) to move toward the housing walls, causing needles (604a, 604b) to pierce the housing wall and extend into tissue. The pressurized fluid is delivered to each second chamber (607a, 607b) via a lumen (609), pushing plungers (606a, 606b) forward and forcing the therapeutic agent out of the chambers (605a, 605b) through the needles (604a, 604b) into the tissue. It should be noted that the needles can be positioned at different angles with respect to the housing wall, depending on a desired application.

In order to position the delivery probe back into the inactivated position, the piezo-electric stack (608) is contracted, which causes the scissor-like delivery mechanism (602) to close, bringing the needles (604a, 604b) back within the housing.

This embodiment of the present invention has several advantages. First, the use of the piezo-electric stack allows for a very precise control over a position of the needles and a depth of incision, as the stack can be expanded and contracted in very small increments. Further, by making the upper arms of the scissor-like delivery mechanism longer than the lower arms, it is possible to extend the needles much further out of the housing, thereby facilitating delivery of the therapeutic agent in larger bodily lumens.

Figure 9A:
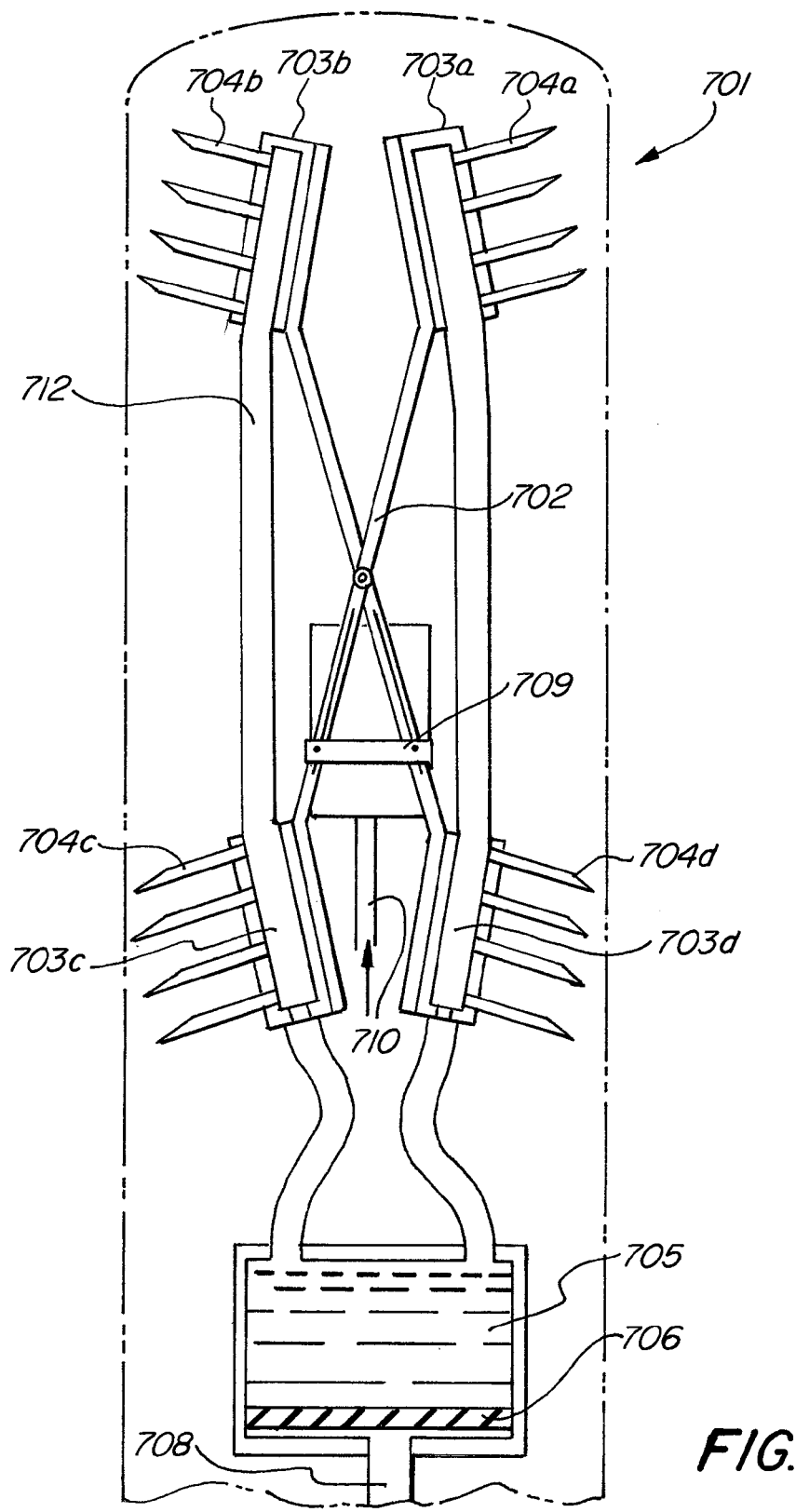
Figure 9B:
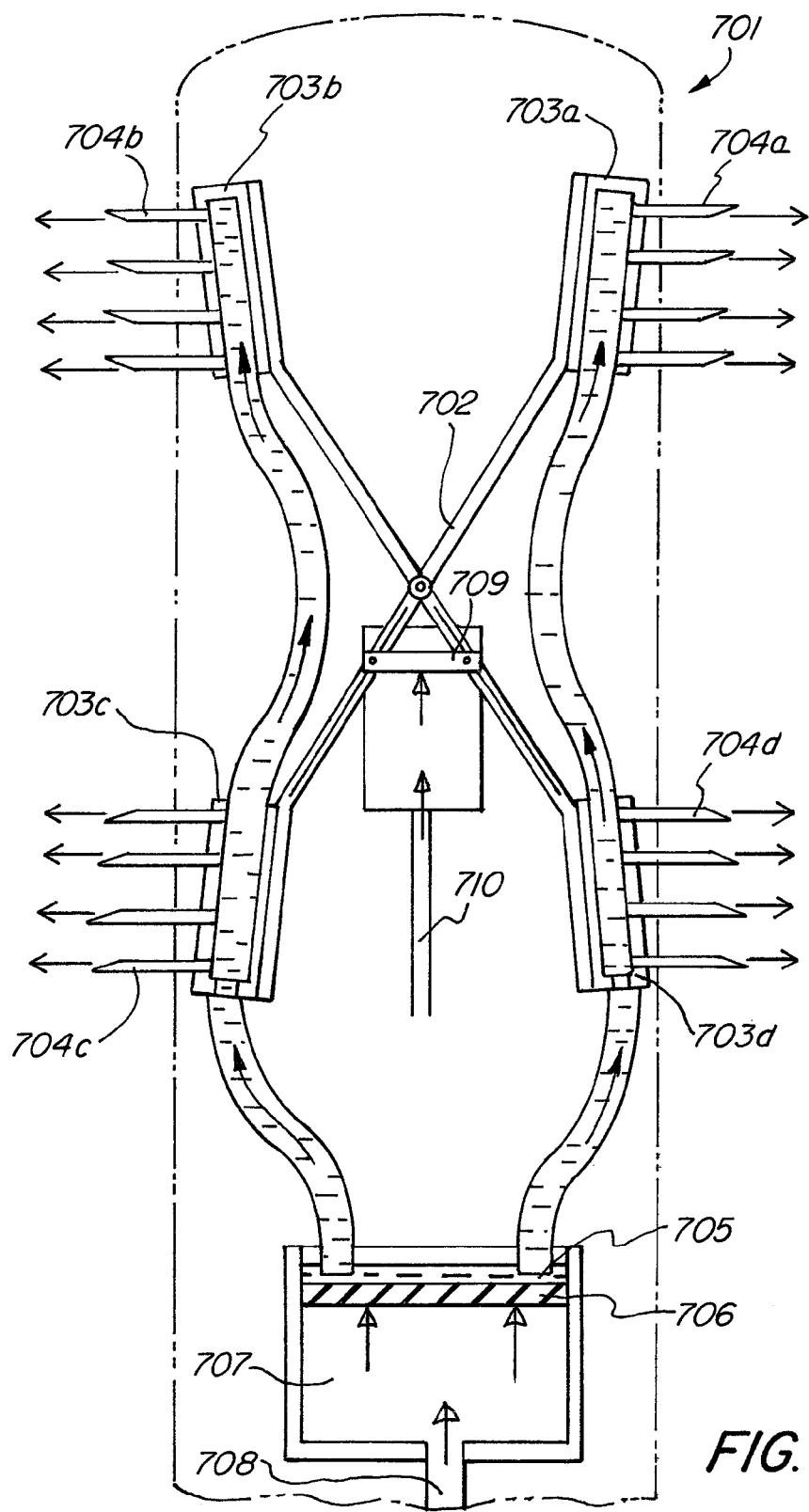

FIGS. 9A and 9B illustrate yet another embodiment of the present invention. In this embodiment of the delivery probe (701), the scissor-like delivery mechanism (702) includes four delivery capsules (703a, 703b, 703c, and 703d) positioned on each upper arm and each lower arm of the scissor-like delivery mechanism (702). Each delivery capsule has a plurality of needles (704a, 704b, 704c, and 704d), or any other suitable delivery mechanism, in fluid communication with a drug containing chamber (705). In this embodiment, each delivery capsule (703a, 703b, 703c, and 703d) is connected with the drug containing chamber (705) by tubing, which is rigidly attached to the arms of the scissor-like delivery mechanism in the areas adjacent to the delivery capsules, but is flexible in the areas between the delivery capsules to allow for movement of the capsules. The delivery probe (701) further includes a second chamber (707) fluidly isolated from the drug containing chamber (705) by a slidable plunger (706). The delivery mechanism (702) is actuated by a piston (709) slidably attached to the lower arms of the delivery mechanism (702).

When in inactivated position, shown in FIG. 9A, the scissor-like delivery mechanism (702) is in a closed position such that the needles (704a, 704b, 704c, and 704d) are housed within the delivery probe. The pressurized fluid is supplied through a lumen (710) to actuated the piston (709), which slides forward, thereby causing the scissor-like delivery mechanism (702) to open, as shown in FIG. 9B. Opening of the delivery mechanism (702) causes the needles (704a, 704b, 704c, and 704d) to extend out of the delivery probe housing and into the surrounding tissue. Then, the pressurized fluid is supplied to the chamber (707) via a lumen (708), causing the plunger (706) to move forward, forcing the therapeutic agent out of the chamber (705), through the needles (704a, 704b, 704c, and 704d) and into the tissue. In order to remove the delivery probe (701) from a patient's body, a vacuum is supplied through the lumen (710), causing the piston (709) to move back and to pull the scissor-like delivery mechanism (702) back into a linear alignment, thereby retracting the needles (704a, 704b, 704c, and 704d) into the housing.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A delivery probe for delivering a therapeutic agent to tissue comprising:
    a housing;
    a sleeve disposed in said housing;
    at least one delivery capsule for accommodating the agent to be delivered;
    wherein at least a portion of said capsule is movably arranged within said sleeve to form an actuation chamber, such that said capsule moves from a first position to a second position when at least one of a fluid and a vacuum are supplied to the actuation chamber;
    at least one delivery device in fluid communication with said at least one capsule; and
    a sliding member for forcing the agent out of said capsule via the delivery device;
    wherein said sliding member is adapted to force the agent out of said at capsule regardless of whether fluid or vacuum are supplied to the actuation chamber.

2. The delivery probe according to claim 1, wherein said at least one delivery capsule comprises a first chamber for accommodating the therapeutic agent to be delivered and a second chamber fluidly isolated from said first chamber by said sliding member slidably disposed in the capsule.

3. The delivery probe according to claim 2, further comprising a delivery chamber provided in said housing in fluid communication with said second chamber.

4. The delivery probe according to claim 3, wherein fluid is supplied by a fluid source connected to at least one of said actuation chamber and delivery chamber.

5. The delivery probe according to claim 4, wherein said fluid source is a pump.

6. The delivery probe according to claim 5, wherein said pump is an electro-pneumatic pump.

7. The delivery probe according to claim 5, wherein said pump includes a processor that controls the supply of fluid based on at least one predetermined parameter.

8. The delivery probe according to claim 4, wherein said fluid source further comprises a vacuum source.

9. The delivery probe according to claim 3, wherein said sliding member is movable by supplying the fluid to said delivery chamber.

10. The delivery probe according to claim 2, wherein said at least one delivery device is in fluid communication with said first chamber.

11. The delivery probe according to claim 2, wherein said actuation chamber is fluidly isolated from said delivery chamber and said at least one capsule.

12. The delivery probe according to claim 1, wherein said at least one delivery device is a needle.

13. The delivery probe according to claim 1, wherein at least one wall of said housing includes a membrane pierceable by said at least one delivery device.

14. The delivery probe according to claim 1, wherein said at least one delivery device is enclosed by said housing when in the inactivated position.

15. The delivery probe according to claim 1, wherein said at least one delivery device extends beyond a distal end of said housing when in the activated position.

16. The delivery probe according to claim 1, wherein said fluid is a gas.

17. The delivery probe according to claim 1, further comprising at least one imaging marker.

18. The delivery probe according to claim 1, further comprising at least one connector for connection to a catheter.

19. The delivery probe according to claim 1, wherein said at least one delivery device comprises at least one sensor for measuring at least one parameter associated with the tissue.

20. A delivery probe for delivering a therapeutic agent to tissue comprising: a housing;
    at least one delivery capsule movably arranged within said housing, said at least one capsule having a first chamber for containing the agent to be delivered and a second chamber sealed from said first chamber by a piston slidably disposed in the capsule;
    at least one delivery device in fluid communication with said first chamber; a delivery chamber provided in said housing in fluid communication with said second chamber; and
    an actuation chamber fluidly isolated from said delivery chamber;
    wherein said at least one delivery device moves between an activated position and an inactivated position in response to a supply of fluid or vacuum to said actuation chamber; and
    wherein said piston moves from first position to a second position in response to a different supply of fluid to said delivery chamber, which then enters the second chamber through openings and pushes on the piston.

21. The delivery probe according to claim 20, wherein said actuation chamber further comprises an inflatable balloon.

22. The delivery probe according to claim 20, wherein said at least one delivery device extends beyond at least one sidewall of said housing when in the activated position.

23. The delivery probe according to claim 20, wherein said at least one capsule comprises a first delivery capsule and a second delivery capsule, wherein said actuation chamber is positioned between the first and second delivery capsules.

24. The delivery probe according to claim 20, wherein said housing comprises an expansion apparatus affixed to an outer wall of said housing.

25. A catheter assembly for delivering a therapeutic agent to tissue comprising:
 a shaft having a first lumen and a second lumen;
 a fluid source; and
 a delivery probe positioned at a distal end of said shaft, comprising
  a housing having a delivery chamber;
  a sleeve disposed in said housing;
  at least one delivery capsule for accommodating the agent to be delivered;
  wherein at least a portion of said capsule is movably arranged within said sleeve to form an actuation chamber, such that said capsule moves from a first position to a second position when at least one of a fluid and a vacuum are supplied to the actuation chamber;
  at least one delivery device in fluid communication with said capsule;
  a sliding member for delivering the agent out of said capsule via the delivery device to the tissue;
  wherein said sliding member is adapted to force the agent out of said capsule regardless of whether fluid or vacuum are first supplied to the actuation chamber;
  wherein the first lumen is in fluid communication with said actuation chamber and a first port of said fluid source, and the second lumen is in fluid communication with said delivery chamber and a second port of said fluid source.

26. The catheter assembly according to claim 25, further comprising at least one guidewire disposed in said shaft.

27. The catheter assembly according to claim 25, further comprising an imaging device positioned at said distal end of said shaft for viewing the tissue.

28. The catheter assembly according to claim 25, further comprising a control device positioned at a proximal end of said shaft and connected to said delivery probe for actuation of the probe.

* * * * *